United States Patent [19]
Hamley et al.

[11] Patent Number: 6,100,246
[45] Date of Patent: Aug. 8, 2000

[54] SPIRO-PIPERIDINE DERIVATIVES AS INHIBITORS OF NITRIC OXIDE SYNTHASE

[75] Inventors: Peter Richard Hamley, Rothley; Thomas McInally; Alan Charles Tinker, both of Loughborough, all of United Kingdom

[73] Assignee: Astra Pharmaceuticals Limited, Herts, United Kingdom

[21] Appl. No.: 09/068,469

[22] PCT Filed: Apr. 7, 1998

[86] PCT No.: PCT/SE98/00642

§ 371 Date: May 8, 1998

§ 102(e) Date: May 8, 1998

[87] PCT Pub. No.: WO98/46611

PCT Pub. Date: Oct. 22, 1998

[30] Foreign Application Priority Data

Apr. 15, 1997 [SE] Sweden ................................. 9701396

[51] Int. Cl.$^7$ .................................. A01N 43/58
[52] U.S. Cl. .................... 514/89; 514/227.5; 514/229.5; 544/6; 544/71
[58] Field of Search ........................... 544/6, 71; 546/19; 514/227.2, 229.5, 89

[56] References Cited

U.S. PATENT DOCUMENTS 3,686,187 8/1972 Cole et al. ........................ 260/293.79
4,092,414 5/1978 Cragoe, Jr. et al. ..................... 544/70

FOREIGN PATENT DOCUMENTS 0 189 370 A2 1/1986 European Pat. Off. .
0 624 567 A2 5/1994 European Pat. Off. .

OTHER PUBLICATIONS

Chemical Abstracts, Arch. Dermatol. Res., vol. 287, pp. 567–571 (1995).
Förstermann et al, "Induced RAW 264.7 macrophages express soluble and particulate nitric oxide . . . ," Eur. J. Pharmacol., vol. 225, pp. 161–165 (1992).
Macdonald et al, "Chapter 23: Nitric Oxide Synthase Inhibitors," Ann. Rep. Med. Chem., vol. 31, pp. 221–230 (1996).
J. Heterocyclic Chem., vol. 29, pp. 779–786 (1982).*
Bull. Chem. Soc. Japan, vol. 33, pp. 575–578 (1960).*

*Primary Examiner*—Mukund J. Shah
*Assistant Examiner*—V Balasubramanian
*Attorney, Agent, or Firm*—Nixon & Vanderhye

[57] ABSTRACT

There are provided novel compounds of formula (I)

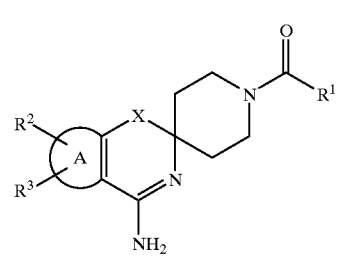

wherein

A represents a benzo ring; a six membered heterocyclic aromatic ring containing 1 to 3 nitrogen atoms; or a five membered heterocyclic aromatic ring containing 1 to 3 heteroatoms which may be the same or different and are selected from O, N and S; and $R^1$, $R^2$, $R^3$ and X are as defined in the Specification and pharmaceutically acceptable salts thereof and enantiomers and tautomers thereof; together with processes for their preparation, compositions containing them and their use in therapy. The compounds are inhibitors of nitric oxide synthase and are thereby particularly useful in the treatment and prophylaxis of inflammatory disease and pain.

14 Claims, No Drawings

SPIRO-PIPERIDINE DERIVATIVES AS INHIBITORS OF NITRIC OXIDE SYNTHASE

FIELD OF THE INVENTION

The present invention relates to novel compounds, as well as related aspects including processes for the preparation of the compounds, compositions containing them and their use as pharmaceuticals. There are also provided chemical intermediates useful for the production of the compounds.

BACKGROUND OF THE INVENTION

Nitric oxide is produced in mammalian cells from L-arginine by the action of specific nitric oxide synthases (NOSs). These enzymes fall into two distinct classes—constitutive NOS (cNOS) and inducible NOS (iNOS). At the present time, two constitutive NOSs and one inducible NOS have been identified. Of the constitutive NOSs, an endothelial enzyme (ecNOS) is involved with smooth muscle relaxation and the regulation of blood pressure and blood flow, whereas the neuronal enzyme (ncNOS) serves as a neurotransmitter and appears to be involved in the regulation of various biological functions such as cerebral ischaemia. Inducible NOS has been particularly implicated in the pathogenesis of inflammatory diseases. Regulation of these enzymes should therefore offer considerable potential in the treatment of a wide variety of disease states (J. E. Macdonald, Ann. Rep. Med. Chem., 1996, 31, 221–230).

DISCLOSURE OF THE INVENTION

According to the invention, there is provided a compound of formula (I):

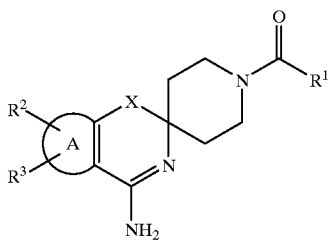

(I)

wherein

A represents a benzo ring; a six membered heterocyclic aromatic ring containing 1 to 3 nitrogen atoms; or a five membered heterocyclic aromatic ring containing 1 to 3 heteroatoms which may be the same or different and are selected from O, N and S;

$R^2$ and $R^3$ independently represent hydrogen, C1 to 6 alkyl, C1 to 6 alkoxy, C1 to 6 alkylthio, halogen, hydroxy or amino;

$R^1$ represents (i) phenyl; a six membered heterocyclic aromatic ring containing 1 to 3 nitrogen atoms; or a five membered heterocyclic aromatic ring containing 1 to 3 heteroatoms which may be the same or different and are selected from O, N and S, the phenyl or heterocyclic aromatic ring being optionally substituted by C1 to 6 alkyl, C1 to 6 alkoxy, C1 to 6 alkylthio, C2 to 6 alkenyl, C2 to 6 alkynyl, C1 to 6 haloalkyl, C2 to 12alkoxyalkyl, C2 to 12 alkylthioalkyl, amino, halogen, hydroxy, cyano or nitro; or (ii) $OR^4$, where $R^4$ represents C1 to 6 alkyl, C2 to 6 alkenyl, C2 to 6 alkynyl, C1 to 6 haloalkyl, C2 to 12 alkoxyalkyl, C2 to 12 alkylthioalkyl, C7 to 12 arylalkyl, C7 to 12 aryloxyalkyl or halogen;

X represents $CH_2$, CO, O or $S(O)_n$ where n represents an integer from 0 to 2; and pharmaceutically acceptable salts, enantiomers, racemates and tautomers thereof.

The invention further provides a process for the preparation of such compounds or a pharmaceutically acceptable salt, enantiomer, racemate or tautomer thereof.

According to the invention there is also provided a compound of formula (I), or a pharmaceutically acceptable salt, enantiomer, racemate or tautomer thereof, for use as a medicament.

Another aspect of the invention provides the use of a compound of formula (I) or a pharmaceutically acceptable salt, enantiomer, racemate or tautomer thereof, in the manufacture of a medicament, for the treatment or prophylaxis of diseases or conditions in which inhibition of nitric oxide synthase activity is beneficial.

A more particular aspect of the invention provides the use of a compound of formula (I) or a pharmaceutically acceptable salt, enantiomer, racemate or tautomer thereof, in the manufacture of a medicament, for the treatment or prophylaxis of inflammatory disease.

According to the invention, there is also provided a method of treating, or reducing the risk of, diseases or conditions in which inhibition of nitric oxide synthase activity is beneficial which comprises administering to a person suffering from or at risk of, said disease or condition, a therapeutically effective amount of a compound of formula (I) or a pharmaceutically acceptable salt, enantiomer, racemate or tautomer thereof.

More particularly, there is also provided a method of treating, or reducing the risk of, inflammatory disease in a person suffering from or at risk of, said disease, wherein the method comprises administering to the person a therapeutically effective amount of a compound of formula (I) or a pharmaceutically acceptable salt, enantiomer, racemate or tautomer thereof.

The compounds of the present invention may also be used advantageously in combination with a second pharmaceutically active substance, particularly in combination with a selective inhibitor of the inducible isoform of cyclooxygenase (COX-2). Thus, in a further aspect of the invention there is provided the use of a compound of formula (I) or a pharmaceutically acceptable salt, enantiomer, racemate or tautomer thereof, in combination with a COX-2 inhibitor for the treatment of inflammation, inflammatory disease and inflammatory related disorders. And there is also provided a method of treating, or reducing the risk of, inflammation, inflammatory disease and inflammatory related disorders in a person suffering from or at risk of, said disease or condition, wherein the method comprises administering to the person a therapeutically effective amount of a compound of formula (I) or a pharmaceutically acceptable salt, enantiomer, racemate or tautomer thereof in combination with a COX-2 inhibitor.

Preferably, A represents a thieno ring.

Preferably, X represents $CH_2$ or O.

Especially preferred compounds of the invention include:
ethyl 4-amino-5-fluorospiro[2H-(1,3)-benzoxazine-2,4'-piperidine]-1'-carboxylate;
ethyl 4'-aminospiro[piperidine-4,6'(7'H)-thieno[3,2-c]pyridine]-1-carboxylate;
ethyl 7'-aminospiro[piperidine-4,5'(4'H)-thieno[2,3-c]pyridine]-1-carboxylate;

and pharmaceutically acceptable salts, enantiomers or tautomers thereof.

Unless otherwise indicated, the term "C1 to 6 alkyl" referred to herein denotes a straight or branched chain alkyl group having from 1 to 6 carbon atoms or a cyclic alkyl group having from 3 to 6 carbon atoms. Examples of such groups include methyl, ethyl, n-propyl, i-propyl, n-butyl, i-butyl, t-butyl, cyclopentyl and cyclohexyl.

Unless otherwise indicated, the term "C2 to 6 alkenyl" referred to herein denotes a straight or branched chain alkyl group having from 2 to 6 carbon atoms and including one double bond or a cyclic alkyl group having from 3 to 6 carbon atoms and including one double bond. Examples of such groups include ethenyl, 1- and 2-propenyl, 2-methyl-2-propenyl, 2-butenyl, cyclopentenyl and cyclohexenyl.

Unless otherwise indicated, the term "C2 to 6 alkynyl" referred to herein denotes a straight or branched chain alkyl group having from 2 to 6 carbon atoms and including one triple bond. Examples of such groups include ethynyl, 1- and 2-propynyl and 2-butynyl.

Unless otherwise indicated, the term "C1 to 6 alkoxy" referred to herein denotes a straight or branched chain alkoxy group having from 1 to 6 carbon atoms. Examples of such groups include methoxy, ethoxy, n-propoxy, i-propoxy, n-butoxy, i-butoxy, s-butoxy and t-butoxy.

Other groups, for example, alkylthio, haloalkyl, alkoxyalkyl, alkylthioalkyl, are to be interpreted similarly.

The process mentioned above, for the preparation of compounds of the invention, or a pharmaceutically acceptable salt, enantiomer, racemate or tautomer thereof comprises:

(a) reaction of a compound of formula (II)

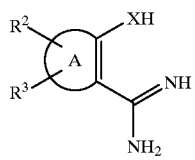

(II)

wherein A, $R^2$ and $R^3$ are as defined above, and X represents O or S, with a compound of formula (III) or an acetal derivative thereof $$R^5COR^6$$ (III)

wherein $R^5$ and $R^6$ together represent $(CH_2)_2 \cdot Z \cdot (CH_2)_2$, Z representing $N(COR^1)$ and $R^1$ being as defined above; or (b) reaction of a compound of formula (IV) or (IV')

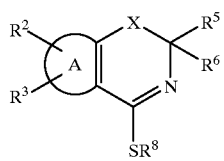

(IV)

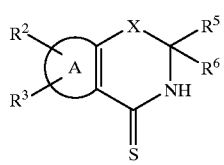

(IV')

wherein A, X, $R^2$ and $R^3$ are as defined above, $R^5$ and $R^6$ are as defined in option (a), and $R^8$ represents an alkyl group;

with ammonia or an equivalent thereof; or (c) deprotection of a compound of formula (I) in which one or more nitrogen atoms and/or another atom is protected; or (d) reaction of a compound of formula (V)

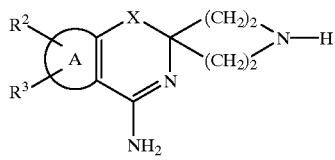

(V)

wherein A, X, $R^2$ and $R^3$ are as defined above, with a compound of formula (VI)

$$Z—L$$ (VI)

wherein Z represents $COR^1$, $R^1$ being as defined above, and L is a leaving group; or (e) preparation of a compound of formula (I) in which X represents $S(O)_n$ and n is 1 or 2, by oxidation of a corresponding compound wherein X represents S; and where desired or necessary converting the resultant compound of formula (I), or another salt thereof, into a pharmaceutically acceptable salt thereof, or vice versa, and where desired converting the resultant compound of formula (I) into an optical isomer thereof.

In process (a), the reaction of compounds of formulae (II) and (III) may be performed by stirring the reactants in an inert solvent at a suitable temperature, generally between room temperature and the boiling temperature of the solvent, for a period of up to 72 hours, or until reaction is complete. We have found that it is often convenient to use the compounds of formula (III) in a protected form, for example as an acetal such as the diethoxy acetal. The process is then preferably carried out in the presence of an acid catalyst. The required acetals may be formed by reacting an unprotected compound of formula (III) with an alcohol such as ethanol using methods that are well known to those skilled in the art.

In process (b), the reaction may be performed by bubbling ammonia gas through a solution of the compound of formula (IV) or (IV') in an inert polar solvent. Alternatively, the reaction may be performed by treating a solution of the compound of formula (IV) or (IV') in a polar protic solvent with aqueous ammonia, ammonia in acetonitrile or with methanolic ammonia or by treating the compound of formula (IV) or (IV') with ammonium iodide and ammonia in alcohol solution.

In process (c), protecting groups for amines include alkyl, aralkyl, acyl, acyl sulphonyl, aryl sulphonyl and trialkylsilyl. When the protecting group is trialkylsilyl, this group may be removed by hydrolysis using, for example, tetra-n-butylammonium fluoride. Other protecting groups and further details of processes for their removal may be found by reference to the standard text "Protecting Groups in Organic Synthesis", 2nd Edition (1991) by Greene and Wuts.

In process (d), the reaction may be performed by combining the reactants in an inert solvent at a suitable temperature in the presence of a base, for example, pyridine. Although a number of standard leaving groups L are suitable, we prefer that L represents a halogen, especially chlorine or bromine.

In process (e), the oxidation may be performed using, for example, m-chloroperbenzoic acid or oxone®.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

Salts of compounds of formula (I) may be formed by reacting the free base, or a salt, enantiomer or tautomer thereof, with one or more equivalents of the appropriate acid. The reaction may be carried out in a solvent or medium in which the salt is insoluble or in a solvent in which the salt is soluble, for example water, dioxane, ethanol, tetrahydrofuran or diethyl ether, or a mixture of solvents, which may be removed in vacuo or by freeze drying. The reaction may also be a metathetical process or it may be carried out on an ion exchange resin.

Novel intermediates of formulae (II), (IV), (IV') and (V) form another aspect of the invention.

Compounds of formula (II) may be prepared by reduction of a compound of formula (VII)

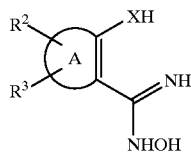

(VII)

wherein A, X, $R^2$ and $R^3$ are as defined above.

This reduction process may be performed by treating the compound of formula (VII) with hydrogen in the presence of palladium on carbon or rhodium on alumina or Raney nickel at elevated temperature and pressure, typically 65° C. and 30 atmospheres pressure.

Compounds of formula (VII) may be prepared by reaction of a compound of formula (VIII)

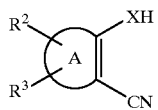

(VIII)

wherein A, X, $R^2$ and $R^3$ are as defined above, with hydroxylamine hydrochloride.

In this reaction, the two reactants may be heated together in the presence of a base, such as sodium methoxide, in methanol.

As an alternative method for the preparation of compounds of formula (II), a compound of formula (VIII) may be treated with a primary alcohol such as ethanol in the presence of acid, and then subsequently treated with ammonium chloride to yield the compound of formula (II).

As a further alternative method for the preparation of compounds of formula (II), a compound of formula (IX)

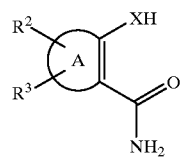

(IX)

wherein A, X, $R^2$ and $R^3$ are as defined above, may be treated with ammonia.

The reaction will take place under standard conditions, although a preactivation step is normally necessary, for example, using Meerwein's reagent.

Compounds of formula III, VIII and IX are either known or may be made by conventional methods known per se.

Compounds of formula (IV) may be prepared by reacting a compound of formula (X)

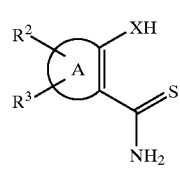

(X)

wherein A, X, $R^2$ and $R^3$ are as defined above, with a compound of formula (III) in the presence of an alkyl iodide.

The conditions for this reaction will be similar to those described above for process (a).

Compounds of formula (X) may be prepared by treating a compound of formula (IX) with Lawesson's reagent.

Compounds of formula (II) may also be prepared by converting a compound of formula (X) into the corresponding alkylthio derivative by treatment with an alkyl halide (especially an alkyl iodide) and subsequently reacting with ammonia following a process analogous to that of process (b) above.

Intermediate compounds may be prepared and used as such or in protected form. Protecting groups and details of processes for their removal may be found by reference to the standard text "Protecting Groups in Organic Synthesis", 2nd Edition (1991) by Greene and Wuts.

The compounds of the invention and intermediates thereto may be isolated from their reaction mixtures and, if necessary further purified, by using standard techniques.

The compounds of formula (I) may exist in enantiomeric forms. Therefore, all enantiomers, diastereomers, racemates and mixtures thereof are included within the scope of the invention. The various optical isomers may be isolated by separation of a racemic mixture of the compounds using conventional techniques, for example fractional crystallisation or HPLC.

Intermediate compounds may also exist in enantiomeric forms and may be used as purified enantiomers, diastereomers, racemates or mixtures thereof.

The compounds of formula (I) may exist in alternative tautomeric forms. Compounds of formula (I) are provided in another tautomeric form or as a mixture thereof.

The compounds of formula (I), and their pharmaceutically acceptable salts, enantiomers, racemates and tautomers, are useful because they possess pharmacological activity in animals. In particular, the compounds are active as inhibitors of the enzyme nitric oxide synthase. More particularly, they are inhibitors of the inducible isoform of the enzyme nitric oxide synthase present in macrophages and as such are expected to be useful in therapy, for example, as anti-inflammatory agents.

The compounds and their pharmaceutically acceptable salts, enantiomers, racemates and tautomers are indicated for use in the treatment or prophylaxis of diseases or conditions in which synthesis or oversynthesis of nitric oxide synthase forms a contributory part. In particular, the compounds are indicated for use in the treatment of inflammatory conditions in mammals, including man.

Conditions that may be specifically mentioned are:
osteoarthritis, rheumatoid arthritis, rheumatoid spondylitis, gouty arthritis and other arthritic conditions, inflamed joints;
eczema, psoriasis, dermatitis or other inflammatory skin conditions such as sunburn;
inflammatory eye conditions including uveitis and conjunctivitis;
lung disorders in which inflammation is involved, for example, asthma, bronchitis, pigeon fancier's disease, farmer's lung, acute respiratory distress syndrome;
bacteraemia, endotoxaemia (septic shock), aphthous ulcers, gingivitis, pyresis, pain and pancreatitis;
conditions of the gastrointestinal tract including Crohn's disease, atrophic gastritis, gastritis varialoforme, ulcerative colitis, coeliac disease, regional ileitis, peptic ulceration, irritable bowel syndrome, damage to the gastrointestinal tract resulting from infections by, for example, *Helicobacter pylori,* or from treatments with non-steroidal anti-inflammatory drugs;
and other conditions associated with inflammation.

The compounds will also be useful in the treatment and alleviation of acute or persistent inflammatory or neuropathic pain or pain of a central origin.

The compounds of formula (I) and their pharmaceutically acceptable salts, enantiomers, racemates and tautomers may also be useful in the treatment or prophylaxis of diseases or conditions in addition to those mentioned above. For example, the compounds may be useful in the treatment of atherosclerosis, cystic fibrosis, hypotension associated with septic and/or toxic shock, in the treatment of dysfunction of the immune system, as an adjuvant to short term immunosuppression in organ transplant therapy, in the treatment of vascular complications associated with diabetes and in cotherapy with cytokines, for example TNF or interleukins.

The compounds of formula (I) may also show inhibitory activity against the neuronal isoform of nitric oxide synthase. Thus they may also be useful in the treatment of hypoxia, for example in cases of cardiac arrest and stroke, neurodegenerative disorders including nerve degeneration and/or nerve necrosis in disorders such as hypoxia, hypoglycaemia, epilepsy, and in external wounds (such as spinal cord and head injury), hyperbaric oxygen convulsions and toxicity, dementia, for example pre-senile dementia, Alzheimer's disease and AIDS-related dementia, Sydenham's chorea, Parkinson's disease, Tourette's Syndrome, Huntington's disease, Amyotrophic Lateral Sclerosis, Korsakoff's disease, imbecility relating to a cerebral vessel disorder, sleeping disorders, schizophrenia, depression, autism, seasonal affective disorder, jet-lag, depression or other symptoms associated with Premenstrual Syndrome (PMS), anxiety and septic shock. Compounds of formula (I) may also be expected to show activity in the prevention and reversal of tolerance to opiates and diazepines, treatment of drug addiction, treatment of migraine and other vascular headaches, neurogenic inflammation, in the treatment of gastrointestinal motility disorders, cancer and in the induction of labour.

For the above mentioned therapeutic indications, the dosage administered will, of course, vary with the compound employed, the mode of administration and the treatment desired. However, in general, satisfactory results are obtained when the compounds are administered at a dosage of the solid form of between 1 mg and 2000 mg per day.

The compounds of formula (I), and pharmaceutically acceptable derivatives thereof, may be used on their own, or in the form of appropriate pharmaceutical compositions in which the compound or derivative is in admixture with a pharmaceutically acceptable adjuvant, diluent or carrier. Administration may be by, but is not limited to, enteral (including oral, sublingual or rectal), intranasal, intravenous, topical or other parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988. The pharmaceutical composition preferably comprises less than 80% and more preferably less than 50% of a compound of formula (I), or a pharmaceutically acceptable salt, enantiomer, racemate or tautomer thereof.

There is also provided a process for the preparation of such a pharmaceutical composition which comprises mixing the ingredients.

The compounds of formula (I), and pharmaceutically acceptable derivatives thereof, may also be advantageously used in combination with a COX-2 inhibitor. Particularly preferred COX-2 inhibitors are Celecoxib and MK-966. The NOS inhibitor and the COX-2 inhibitor may either be formulated together within the same pharmaceutical composition for administration in a single dosage unit, or each component may be individually formulated such that separate dosages may be administered either simultaneously or sequentially.

The invention is illustrated, but in no way limited, by the following examples:

PREPARATION 1

Ethyl 1-oxa-6-azaspiro[2,5]octane-6-carboxylate

A solution of 47% sodium hydroxide (15 ml), ethyl 4-oxopiperidine-1-carboxylate (4.53 ml, 30 mmol), trimethylsulphonium methanesulphonate (7.36 g, 39 mmol) (*Syn. Comm.,* 1985, 15, 749) and dichloromethane (30 ml) was heated to 50° C. for 16 h, cooled, diluted with water (30 ml), and extracted with dichloromethane. The combined extracts were dried over sodium sulphate and evaporated. The residue was purified by flash column chromatography on silica, eluting with 2% methanol/dichloromethane to give the product as a mobile yellow oil (4.0 g), MS (+EI)$^m$/z 185; $^1$H NMR (360 MHz) (CDCl$_3$) 4.15 (2H, q, J7.1 Hz), 3.78 (2H, brs), 3.46 (1H, ddd, J3.7, 9.6, 13.3 Hz), 2.71 (2H, s), 1.87–1.79 (2H, m), 1.49–1.43 (2H, m), 1.28 (3H, t, J7.1 Hz).

EXAMPLE 1

Ethyl 4-amino-5-fluorospiro[2H-(1,3)-benzoxazine-2,4'-piperidine]-1'-carboxylate (a) 2-Fluoro-6-hydroxybenzamide 2-Fluoro-6-hydoxybenzoic acid (20.0 g, 0.128 mol) and oxalyl chloride (22.3 ml, 0.256 mol) were dissolved in ethyl acetate (300 ml) together with N,N-dimethylformamide (DMF) (2 drops) and the mixture was stirred under an atmosphere of nitrogen for 20 h. The solvent was removed by distillation under reduced pressure leaving the crude acid chloride which was redissolved in ethyl acetate (300 ml) and cooled to 0° C. Concentrated aqueous ammonia (d 0.88, 50 ml) was added dropwise and the mixture was stirred for a further 2 h. The mixture was poured into aqueous sodium bicarbonate solution. The organic phase was separated and the aqueous phase extracted with ethyl acetate (2×200 ml). The combined organic phases were dried (MgSO$_4$) and concentrated leaving the crude compound (10.2 g, 51.5%). Mass spectrum (−ve CI)$^m$/z 154 (M$^+$-H) .

(b) Ethyl 5-fluoro-3,4-dihydro-4-oxospiro[2H-(1,3)-benzoxazine-2,4'-piperidine]-1'-carboxylate The product of step (a) above (10.0 g, 64.5 mmol), ethyl 4-oxopiperidine-1-carboxylate (10.5 ml, 69 mmol) and concentrated sulphuric acid (1 ml) in chloroform (200 ml) were heated at reflux for 6 h. through a Soxhlet apparatus containing anhydrous calcium chloride. After cooling the solution was washed with aqueous sodium bicarbonate, dried (MgSO$_4$) and concentrated under reduced pressure. The residue was purified by flash chromatography on silica gel using ethyl acetate as eluent to give the title lactam as a solid (15.4 g, 77%), m.p. 196–198° C. Mass spectrum (+ve CI)$^m$/z 309 (M$^+$+H).

(c) Ethyl 5-fluoro-3,4-dihydro-4-thioxospiro[2H-(1,3)-benzoxazine-2,4'-piperidine]-1'-carboxylate The product of step (b) above (7.6 g, 25 mmol) and Lawesson's reagent (6.4 g, 16 mmol) in toluene (150 ml) were heated at reflux for 1 h. The mixture was cooled and the precipitate was filtered off, dissolved in ethyl acetate and washed with aqueous sodium bicarbonate. Concentration of the organic solution under reduced pressure gave the title thioamide as a solid (5.1 g., 64%), m.p. 206–207° C. Mass spectrum (+ve CI)$^m$/z 325 (M$^+$+H).

(d) Ethyl 4-amino-5-fluorospiro[2H-(1,3)-benzoxazine-2,4'-piperidine]-1'-carboxylate The product of step (c) above (2.0 g, 6 mmol) was dissolved in an excess of a 7M solution of anhydrous ammonia in methanol and heated at 50° C. for 6 h. After evaporation of the solvent the residue was purified by flash chromatography on silica gel using dichloromethane/methanol (98:2) as eluent to give the title compound as a solid (1.8 g), m.p. 114–116° C. Mass spectrum (+ve CI)$^m$/z 308 (M$^+$+H). Found: C, 58.63; H, 5.84; N, 13.67. Required for $C_{15}H_{18}FN_3O_3$: C, 58.62; H, 5.90; N, 13.67%.

EXAMPLE 2

Ethyl 4'-aminospiro[piperidine-4,6'(7'H)-thieno[3,2-c]pyridine]-1-carboxylate (a) Ethyl 4-hydroxy-4-(2-thienylmethyl)piperidine-1-carboxylate n-Butyllithium (1.46M in hexane, 11.1 ml, 16.2 mmol) was added dropwise to a solution of thiophene (1.33 ml, 16.8 mmol) in THF (60 ml) at −78° C. The solution was warmed to −20° C. and then cooled back to −78° C. After 30 minutes, boron trifluoride etherate (2.1 ml, 16 mmol) was added, followed by the epoxide (Preparation 1) (1.00 g, 5.41 mmol) in THF (10 ml). After 15 minutes the reaction was quenched with water (20 ml) and extracted twice with dichloromethane. The combined extracts were dried over sodium sulphate and then evaporated. The residue was purified by flash column chromatography on silica, eluting with 2% methanol/dichloromethane to give the product as a viscous colourless oil (1.0 g, 70%), MS (+EI)$^m$/z 269; $^1$H NMR (360 MHz) (CDCl$_3$) 7.22–7.17 (1H, m), 6.99 (1H, dd, J3.4, 5.1 Hz), 6.86 (1H, d, J3.4 Hz), 4.12 (2H, q, J7.1 Hz), 3.91 (2H, br s), 3.16 (2H, br s), 2.97 (2H, s), 1.57 (4H, br s), 1.26 (3H, t, J 7.1 Hz).

(b) Ethyl 4'-(ethylthio)spiro[piperidine-4,6'(7'H)-thieno[3,2-c]pyridine]-1-carboxylate Tin(IV) chloride (0.65 ml, 5.56 mmol) was added to a mixture of ethyl thiocyanate (0.72 ml, 8.34 mmol) and the product of Example 2(a) (373 mg, 1.39 mmol) in toluene (7 ml). The solution was heated to reflux for 2 h, cooled, diluted with 10% aqueous sodium hydroxide solution, and extracted twice with ethyl acetate. The combined organic extracts were extracted twice with 4N hydrochloric acid and the combined acid extracts were basified with 10% sodium hydroxide solution and ice. The basic solution was extracted four times with ethyl acetate and the combined organics were dried over sodium sulphate and evaporated to afford a yellow oil (115 mg, 24%), MS (+EI)$^m$/z 338; $^1$H NMR (360 MHz) (CDCl$_3$) 7.12 (1H, d, J5.1 Hz), 7.05 (1H, d, J5.1 Hz), 4.14 (2H, q, J7.1 Hz), 3.91 (2H, br s), 3.48–3.38 (2H, m), 3.07 (2H, q, J 7.4 Hz), 2.76 (2H, s), 1.75 (2H, d, J 12.5 Hz), 1.52 (2H, dt, J4.5, 12.2 Hz), 1.35 (3H, t, J7.3 Hz), 1.26 (3H, t, J7.1 Hz).

(c) Ethyl 4'-aminospiro[piperidine-4,6'(7'H)-thieno[3,2-c]pyridine]-1-carboxylate A mixture of the thioimidate from step (b) above (150 mg, 0.443 mmol), ammonium chloride (64 mg, 0.44 mmol) and ammonia (2N solution in methanol, 1 ml) in ethanol (1 ml) was heated to reflux for 3 h. The cooled solution was diluted with diethyl ether and triturated to give the product hydroiodide salt as beige crystals (112 mg, 60%), m.p. 242–252° C. (decomp.), MS (+EI)$^m$/z 293; $^1$H NMR (360 MHz) (d$_6$-DMSO) 9.26 (2H, br s), 7.69 (1H, d, J 5.4 Hz), 7.65 (I H, d, J 5.4 Hz), 4.05 (2H, q, J 7.0 Hz), 3.48–3.27 (4H, m), 1.72 (4H, t, J 5.5 Hz), 1.84 (3H, t, J 7.1 Hz).

EXAMPLE 3

Ethyl 7'-aminospiro[piperidine-4,5'(4'H)-thieno[2,3-c]pyridine]-1-carboxylate (a) Ethyl 4-hydroxy-4-(3-thienylmethyl)piperidine-1-carboxylate This was prepared by the method of Example 2(a) using 3-thienyllithium, with the exception that the reaction was conducted at −100° C. rather than at −78° C., and after the addition of the epoxide (Preparation 1) the reaction was warmed to −78° C. over 30 minutes. This procedure gave the product as a colourless oil (16%), $^1$H NMR (360 MHz) (CDCl$_3$) 7.32–7.30 (1H, m), 7.06–7.04 (1H, m), 7.01–6.98 (1H, m), 4.12 (2H, q, J7.1 Hz), 4.0–3.8 (2H, br s), 3.2–3.1 (2H, br m), 2.79 (2H, s), 1.6–1.5 (4H, m), 1.26 (3H, t, J 7.1 Hz).

(b) Ethyl 7'-(ethylthio)spiro[piperidine-4,5'(4'H)-thieno[2,3-c]pyridine]-1-carboxylate This was prepared from the product of step (a) above by the method of Example 2(b) to give a yellow oil (30%), MS (+EI)$^m$/z 338.

(c) Ethyl 7'-aminopiro[piperidine-4,5'(4'H)-thieno[2,3-c]pyridine]-1-carboxylate This was prepared from the product of step (b) above by the method of Example 2(c) to give the hydroidodide salt as white crystals, m.p. >230° C., MS (+EI)$^m$/z 294; $^1$H NMR (360 MHz) (d$_6$-DMSO) 8.18(l H, d, J 4.9 Hz), 7.22 (1H, d, J 4.9 Hz), 4.05 (2H, q, J 7.0 Hz), 3.46 (4H, br s), 3.15 (2H, s), 1.71 (4H, br s), 1.18 (3H, t, J7.1 Hz).

Screens

The pharmacological activity of compounds according to the invention was tested using the following screens.

Screen 1

The activity of a compound of formula (I), or a pharmaceutically acceptable salt, enantiomer or tautomer thereof, may be screened for nitric oxide synthase inhibiting activity by a procedure based on that of Forstermann et al., Eur. J. Pharm., 1992, 225, 161–165. Nitric oxide synthase converts $^3$H-L-arginine into $^3$H-L-citrulline which can be separated by cation exchange chromatography and quantified by liquid scintillation counting.

Enzyme is prepared, after induction, from the cultured murine macrophage cell line J774A-1 (obtained from the laboratories of the Imperial Cancer Research Fund). J774A-1 cells are cultured in Dulbecco's Modified Eagles Medium (DMEM) supplemented with 10% foetal bovine serum, 4 mM L-glutamine and antibiotics (100 units/ml penicillin G, 100 mg/ml streptomycin and 0.25 mg/ml amphotericin B). Cells are routinely grown in 225 cm$^3$ flasks containing 35 ml medium kept at 37° C., and in a humidified atmosphere containing 5% $CO_2$.

Nitric oxide synthase is produced by cells in response to interferon-g (IFNg) and lipopolysaccharide (LPS). The medium from confluent culture flasks is removed and replaced with 25 ml (per flask) of fresh medium containing 1 mg/ml LPS and 10 units/ml IFNg. After a period of 17–20 hours in culture, harvesting of cells is accomplished by scraping the cell sheet from the flask surface into the culture medium. Cells are collected by centrifugation (1000 g for 10 minutes) and lysate prepared by adding to the cell pellet a solution containing 50 mM Tris-HCl (pH 7.5 at 20° C.), 10% (v/v) glycerol, 0.1% (v/v) Triton-X-100, 0.1 mM dithiothreitol and a cocktail of protease inhibitors comprising leupeptin (2 mg/ml), soya bean trypsin inhibitor (10 mg/ml), aprotinin (5 mg/ml) and phenylmethylsulphonyl fluoride (50 mg/ml).

For the assay, 25 $\mu$l of substrate cocktail (50 mM Tris-HCl (pH 7.5 at 20° C.), 400 $\mu$M NADPH, 20 $\mu$M flavin adenine dinucleotide, 20 $\mu$M flavin mononucleotide, 4 $\mu$M tetrahydrobiopterin, 12 $\mu$M L-arginine and 0.025 mCi L-[$^3$H] arginine) is added to wells of a 96 well filter plate (0.45 $\mu$M pore size) containing 25 $\mu$l of a solution of test compound in 50 mM Tris-HCl. The reaction is started by adding 50 $\mu$l of cell lysate (prepared as above) and after incubation for 1 hour at room temperature is terminated by addition of 50 $\mu$l of an aqueous solution of 3 mM nitroarginine and 21 mM EDTA.

Labelled L-citrulline is separated from labelled L-arginine using Dowex AG-50W. 150 $\mu$l of a 25% aqueous slurry of Dowex 50W (Na$^+$ form) is added to the assay after which the whole is filtered into 96 well plates. 75 $\mu$l of filtrate is sampled and added to wells of 96 well plates containing solid scintillant. After allowing the samples to dry the L-citrulline is quantified by scintillation counting.

In a typical experiment basal activity is 300 dpm per 75 $\mu$l sample which is increased to 1900 dpm in the reagent controls. Compound activity is expressed as $IC_{50}$ (the concentration of drug substance which gives 50% enzyme inhibition in the assay) and aminoguanidine, which gives an $IC_{50}$ (50% inhibitory concentration) of 10 $\mu$M, is tested as a standard to verify the procedure. Compounds are tested at a range of concentrations and from the inhibitions obtained $IC_{50}$ values are calculated. Compounds that inhibit the enzyme by at least 25% at 100 $\mu$M are classed as being active and are subjected to at least one retest.

The compounds of Examples 1 to 3 were tested in the above screen, and gave $IC_{50}$ values of less than 1 $\mu$M indicating that they are predicted to show useful therapeutic activity.

Screen 2

Compounds also show activity against the human form of induced nitric oxide synthase as can be demonstrated in the following assay.

Enzyme is prepared, after induction, from the cultured human colon adrenocarcinoma cell line DLD1 (obtained from the European Collection of Animal Cell Culture—cell line number 90102540). DLD1 cells are cultured in RPMI 1640 medium supplemented with 10% foetal bovine serum, 4 mM L-glutamine and antibiotics (100 units/ml penicillin G, 100 $\mu$g/ml streptomycin and 0.25 $\mu$g/ml amphotericin B). Cells are routinely grown in 225 cm$^3$ flasks containing 35 ml medium kept at 37° C. and in a humidified atmosphere containing 5% $CO_2$.

Nitric oxide synthase is produced by cells in response to interferon-$\gamma$ (IFN-$\gamma$) and interleukin-1$\beta$ (IL-1$\beta$). The medium from confluent flasks is removed and replaced with 25 ml (per flask) of fresh medium containing 250 units/ml IL-1$\beta$ and 1000 units/ml IFN-$\gamma$. After a period of 17–20 hours in culture, harvesting of cells is accomplished by scraping the cell monolayer from the flask surface into the culture medium. Cells are collected by centrifugation (1000 g for 10 minutes) and lysate prepared by adding to the cell pellet a solution containing 50 mM Tris-HCl (pH 7.5 at 20° C.), 10% (v/v) glycerol, 0.1% (v/v) Triton-X100, 0.1 mM dithiothreitol and a cocktail of protease inhibitors including leupeptin (2 $\mu$g/ml), soya bean trypsin inhibitor (10 $\mu$g/ml), aprotonin (5 $\mu$g/ml) and phenylmethylsulphonyl fluoride (50 $\mu$g/ml).

For the assay, 25 $\mu$l of substrate cocktail (50 mM Tris-HCl (pH 7.5), 400 $\mu$M NADPH, 20 $\mu$M flavin adenine dinucleotide, 20 $\mu$M flavin mononucleotide and 4 $\mu$M tetrahydrobiopterin) is added to the wells of a 96-well plate. Test compounds are preincubated with enzyme by adding together with 40 $\mu$l of cell lysate (prepared as above) and incubating for 1 hour at 37° C. at the end of which period 10 $\mu$l of 30 $\mu$M L-arginine and 0.025 $\mu$Ci of L-[$^3$H]-arginine in 50 mM Tris-HCl is added to start the enzymatic reaction. Incubation is continued for a further 1 hour at 37° C. The reaction is terminated by addition of 50 $\mu$l of an aqueous solution of 3 mNM nitroarginine and 21 mM EDTA.

Labelled L-citrulline is separated from labelled L-arginine using Dowex AG-50W. 120 $\mu$l of a 25% aqueous slurry of Dowex 50W is added to 96 well filter plates (0.45 $\mu$m pore size). To this is added 120 $\mu$l of terminated assay mix. 75 $\mu$l of filtrate is sampled and added to the wells of 96 well plates containing solid scintillant. After allowing the samples to dry the L-citrulline is quantified by scintillation counting.

In a typical experiment basal activity is 300 dpm per 75 $\mu$l sample of reagent controls, which is increased to 3000 dpm in the presence of enzyme. Compound activity is expressed as $IC_{50}$ (the concentration of drug substance which gives 50% enzyme inhibition in the assay) and L-NMMA, which gives an $IC_{50}$ of about 0.4 $\mu$M is tested as a standard to verify the procedure. Compounds are tested at a range of concentrations and from the inhibitions obtained $IC_{50}$ values are calculated.

In this screen compounds of the Examples 1 to 3 give $IC_{50}$ values less than 25 $\mu$m, indicating that they are predicted to show useful therapeutic activity.

What is claimed is:

1. A compound of formula (I)

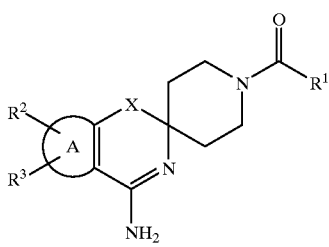

wherein
- A represents a benzo ring; a six membered heterocyclic aromatic ring having 1 to 3 nitrogen atoms, or a five membered heterocyclic aromatic ring having 1 to 3 heteroatoms which may be the same or different and are selected from O, N and S;
- $R^2$ and $R^3$ independently represent hydrogen, C1 to 6 alkyl, C1 to 6 alkoxy, C1 to 6 alkylthio, halogen, hydroxy or amino;
- $R^1$ represents
  - (i) phenyl; a six membered heterocyclic aromatic ring having 1 to 3 nitrogen atoms; or a five membered heterocyclic aromatic ring having 1 to 3 heteroatoms which may be the same or different and are selected from O, N and S, the phenyl or heterocyclic aromatic ring being unsubstituted or substituted by C1 to 6 alkyl, C1 to 6 alkoxy, C1 to 6 alkylthio, C2 to 6 alkenyl, C2 to 6 alkynyl, C1 to 6 haloalkyl, C2 to 12 alkoxyalkyl, C2 to 12 alkylthioalkyl, amino, halogen, hydroxy, cyano or nitro; or
  - (ii) $OR^4$, where $R^4$ represents C1 to 6 alkyl, C2 to 6 alkenyl, C2 to 6 alkynyl, C1 to 6 haloalkyl, C2 to 12 alkoxyalkyl, C2 to 12 alkylthioalkyl, C7 to 12 arylalkyl or C7 to 12 aryloxyalkyl;
- X represents $CH_2$, CO, O or $S(O)_n$ where n represents an integer from 0 to 2; or a pharmaceutically acceptable salt, enantiomer or tautomer thereof.

2. A compound of formula (I), according to claim 1, wherein A represents a thieno ring.

3. A compound of formula (I), according to claim 1, wherein X represents $CH_2$.

4. A compound of formula (I), according to claim 1, wherein X represents O.

5. A compound of formula (I), according to claim 1, wherein A represents a thieno ring and X represents $CH_2$ or O.

6. A compound of formula (I) which is:
ethyl 4-amino-5-fluorospiro[2H-(1,3)-benzoxazine-2,4'-piperidine]-1'-carboxylate;
ethyl 4'-aminospiro[piperidine-4,6'(7'H)-thieno[3,2-c]pyridine]-1-carboxylate;
ethyl 7'-aminospiro[piperidine-4,5'(4'H)-thieno[2,3-c]pyridine]-1-carboxylate;
or a pharmaceutically acceptable salt, enantiomer or tautomer thereof.

7. A pharmaceutical composition comprising a compound of formula (I) according to claim 1, or a pharmaceutically acceptable salt, enantiomer or tautomer thereof, in admixture with a pharmaceutically acceptable adjuvant, diluent or carrier.

8. A method of treating, or reducing the risk of, human diseases or conditions in which inhibition of nitric oxide synthase activity is beneficial which comprises administering a therapeutically effective amount of a compound of formula (I), as defined in claim 1, or a pharmaceutically acceptable salt, enantiomer or tautomer thereof, to a person suffering from, or at increased risk of, such diseases or conditions.

9. A method of treatment according to claim 8 in which it is predominantly inducible nitric oxide synthase that is inhibited.

10. A method of treating, or reducing the risk of, inflammatory disease in a person suffering from, or at risk of, said disease, wherein the method comprises administering to the person a therapeutically effective amount of a compound of formula (I), as defined in claim 1, or a pharmaceutically acceptable salt, enantiomer or tautomer thereof.

11. A method of treatment as claimed in claim 10 wherein the disease is asthma or rheumatoid arthritis.

12. A method of treating, or reducing the risk of, pain in a person suffering from, or at risk of, said condition, wherein the method comprises administering to the person a therapeutically effective amount of a compound of formula (I), as defined in claim 1, or a pharmaceutically acceptable salt, enantiomer or tautomer thereof.

13. A method of treating, or reducing the risk of, inflammatory disease in a person suffering from, or at risk of, said disease, wherein the method comprises administering to the person a therapeutically effective amount of a combination of a compound of formula (I), as defined in claim 1, or a pharmaceutically acceptable salt, enantiomer or tautomer thereof, with a COX-2 inhibitor.

14. A process for the preparation of a compound of formula (I), as defined in claim 1, or a pharmaceutically acceptable salt, enantiomer or tautomer thereof, wherein the process comprises:

(a) reaction of a compound of formula (II)

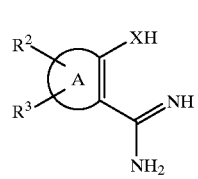

wherein A, $R^2$ and $R^3$ are as defined above, and X represents O or S, with a compound of formula (III) or an acetal derivative thereof $$R^5COR^6 \quad (III)$$

wherein $R^5$ and $R^6$ together represent $(CH_2)_2\text{-}Z\text{-}(CH_2)_2$, Z representing $N(COR^1)$ and $R^1$ being as defined above; or (b) reaction of a compound of formula (IV) or (IV')

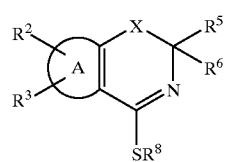

-continued

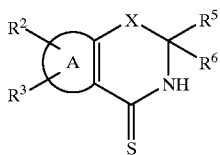

(IV′)

wherein A, X, $R^2$ and $R^3$ are as defined above, $R^5$ and $R^6$ are as defined in option (a), and $R^8$ represents an alkyl group;

with ammonia or an equivalent thereof; or (c) deprotection of a compound of formula (I) in which one or more nitrogen atoms and/or another atom is protected; or (d) reaction of a compound of formula (V)

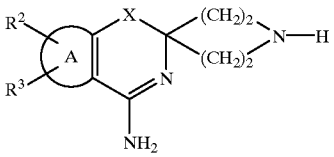

(V)

wherein A, X, $R^2$ and $R^3$ are as defined above, with a compound of formula (VI)

$$Z-L \qquad \text{VI)}$$

wherein Z represents $COR^1$, $R^1$ being as defined above, and L is a leaving group; or (e) preparation of a compound of formula (I) in which X represents $S(O)_n$ and n is 1 or 2, by oxidation of a corresponding compound wherein X represents S;

and where desired or necessary converting the resultant compound of formula (I), or another salt thereof, into a pharmaceutically acceptable salt thereof, or vice versa, and where desired converting the resultant compound of formula (I) into an optical isomer thereof.

\* \* \* \* \*